United States Patent [19]

Loev et al.

[11] Patent Number: 4,621,099

[45] Date of Patent: Nov. 4, 1986

[54] POLYENE COMPOUNDS USEFUL IN THE TREATMENT OF ALLERGIC RESPONSES

[75] Inventors: Bernard Loev, Scarsdale; Wan-Kit Chan, Yorktown Heights, both of N.Y.

[73] Assignee: USV Pharmaceutical Corporation, Tuckahoe, N.Y.

[21] Appl. No.: 778,952

[22] Filed: Sep. 23, 1985

[51] Int. Cl.$^4$ .................................. A61K 31/19
[52] U.S. Cl. ........................ 514/570; 514/381; 514/541
[58] Field of Search .......................... 514/570

Primary Examiner—Stanley J. Friedman

[57] ABSTRACT

Polyene compounds represented by the formula

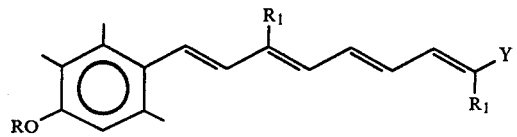

in which

R is H, lower alkyl of from 1 to 8 carbon atoms or aralkyl;

$R_1$ is H or lower alkyl of from 1 to 5 carbon atoms; and

Y is carboxy, alkoxycarbonyl, alkenyloxycarbonyl, aralkoxycarbonyl, tetrazolyl or

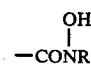

wherein R is H, lower alkyl of from 1 to 8 carbon atoms or aralkyl; and pharmaceutically acceptable salts thereof.

The foregoing compounds have been found active in regulating the formation of lipoxygenase and as such possess therapeutic value in the treatment of inflammatory conditions and allergic responses.

2 Claims, No Drawings

POLYENE COMPOUNDS USEFUL IN THE TREATMENT OF ALLERGIC RESPONSES

BACKGROUND OF THE INVENTION

The present invention relates to polyene compounds and more particularly to arylnonatetraenoic acids and derivatives derived from intermediates represented by the general formula:

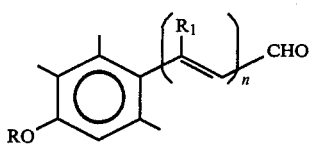

where $R_1$ is H or lower alkyl of from 1 to 5 carbon atoms; R is H, lower alkyl of from 1 to 8 carbon atoms or aralkyl and n is from 0 to 3. A synthesis of 2,3,6-trimethyl-p-anisaldehyde is described in U.S. Pat. No. 4,105,681. The same patent also describes compounds of the formula:

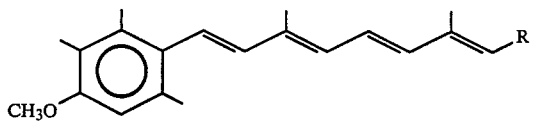

wherein R is formyl, hydroxymethylene, alkoxymethylene, alkanoyloxymethylene, carboxyl, alkoxycarbonyl, alkenyloxycarbonyl, alkynyloxycarbonyl, carbamoyl, mono(lower alkyl)-carbamoyl, di(lower alkyl)-carbamoyl, or N-heterocyclylcarbonyl; and pharmaceutically acceptable salts thereof useful as anti-tumor agents.

A synthesis of 5-(4-methoxy-2,3,6-trimethylphenyl)-3-methyl-2,4-pentadien-1-al is described in U.S. Pat. No. 4,137,246 and Swiss Patnet No. 616,134. A synthesis of 5-(2,3-dimethyl-4-methoxyphenyl)-3-methyl-2,4-pentadien-1-al is described in U.S. Pat. No. 4,534,979. M. P. Reddy, et al. (*Synthesis*, 1980,(10),815–18) describes the synthesis of certain 5-aryl-3-methyl-2(E),4(E)-pentadienals.

SUMMARY OF THE INVENTION

The present invention is directed to polyene compounds of the general formula

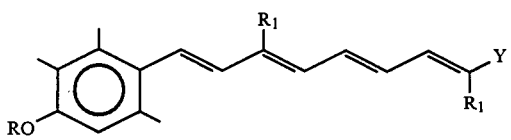

in which

R is H, lower alkyl of from 1 to 8 carbon atoms or aralkyl;

$R_1$ is H or lower alkyl of from 1 to 5 carbon atoms; and

Y is carboxy, alkoxycarbonyl, alkenyloxycarbonyl, aralkoxycarbonyl, tetrazolyl or

wherein R is H, lower alkyl of from 1 to 8 carbon atoms or aralkyl; and pharmaceutically acceptable salts thereof.

DETAILED DESCRIPTION OF THE INVENTION

The general method of preparation utilizes a modified Wittig reaction in which an appropriate aldehyde is treated with a Horner reagent of the formula:

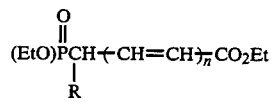

wherein R is H or lower alkyl of from 1 to 5 carbon atoms and n is from 0 to 1.

The esters thus obtained can be converted to acids by hydrolysis.

The aryl polyenoic hydroxamic acids or hydroxamates are prepared by activation of the corresponding acid with an activating agent prior to the treatment with a hydroxylamine. Example of such activating reagents are: oxalyl chloride, phosphorus trichloride, thionyl chloride or 1,1'-carbonyldiimidazole.

An alternate method for the preparation of aryl polyenoic hydroxamic acids or hydroxamates is by reacting the corresponding polyenoic acids with an appropriate hydroxylamine in the presence of a dehydrating agent, such as dicyclohexylcarbodiimide, 1-cyclohexyl-3-(2-morpholinoethyl) carbodimide meta-p-toluenesulfonate or 1-hydroxybenzotriazole.

The preferred methods of synthesizing the compounds of the invention are described in the Examples that follow.

EXAMPLE 1

Ethyl 9-(4-Methoxy-2,3,6-trimethylphenyl)-2,4,6,8-nonatetraenoate

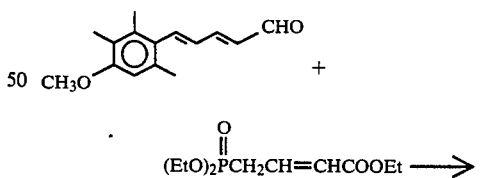

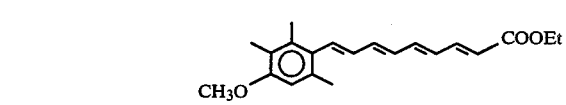

To a suspension of sodium hydride (1.4 g, 50% dispersion in mineral oil) in 30 mL of THF stirred in an ice bath under nitrogen was added dropwise a solution of triethyl phosphonocrotonate (7.8 g, 0.03 mol) in 30 mL of THF. The resulting mixture was stirred at 0° C. for additional ½ hr and a solution of 5-(4-methoxy-2,3,6-trimethylphenyl)penta-2,4-dienal (4.8 g, 0.02 mol) in 15 mL of THF was added rapidly. The mixture was stirred at room temperature for 18 hrs. Brine (50 mL) was added to the mixture, followed by 200 mL of ethyl acetate. The layers were separated. The organic layer was washed with brine, dried (Na$_2$SO$_4$) and concentrated in vacuo to give 6.1 g of the crude product as a yellow oil. This material was used in the reaction described in Example 2 without further purification.

EXAMPLE 2

9-(4-Methoxy-2,3,6-trimethylphenyl)-2,4,6,8-nonatetraenoic Acid

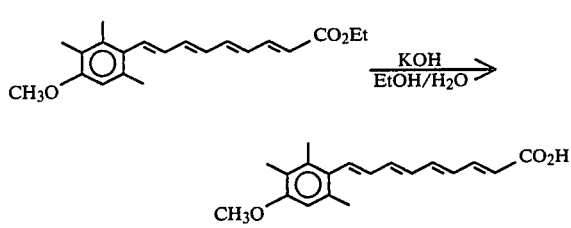

A solution of 6.1 g (0.019 mol) of the ethyl ester of Example 1 was dissolved in 15 mL of ethanol and a solution of KOH (1.6 g, 0.028 mol) in 5 mL of ethanol and 1 mL of water was added. The mixture was stirred under nitrogen for 18 hrs and ethanol was evaporated in vacuo. The residue was dissolved in 100 mL of water and the resulting mixture extracted with three 20 mL-portions of ethyl acetate. The organic layers were discarded. The aqueous layer was cooled in an ice bath and acidified to pH 3 with 10N hydrochloric acid. The yellow precipitate was extracted into ethyl acetate, washed with brine and dried. Evaporation of solvent in vacuo afforded a yellow substance. Crystallization from ether gave 0.8 g of the product as yellow crystals: mp 187°–189° C.; MS-298 (m+); UV(MeOH) $\lambda_{max}$ 340 nm.

EXAMPLE 3

9-(4-Methoxy-2,3,6-trimethylphenyl)-7-methyl-2,4,6,8-nonatetraenoic Acid

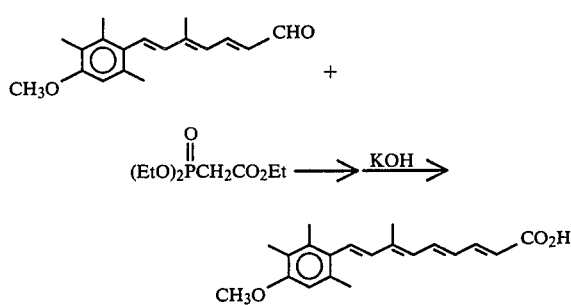

In a manner similar to Example 1, 7-(4-methoxy-2,3,6-trimethylphenyl)-5-methylhepta-2,4,6-trien-1-al (4.7 g, 0.018 mol) was treated with triethyl phosphonoacetate (5.9 g, 0.027 mol) to afford the crude ethyl ester of the title compound as a yellow oil. Subsequent alkaline hydrolysis of this substance by KOH, in a manner similar to Example 2, gave the product as a yellow powder. Crystallization from dimethyl sulfoxide/ethyl ether gave yellow crystals: mp 177°–179° C.; MS (EI): 312 (m+), 297, 251, 237, 150.

EXAMPLE 4

2,7-Dimethyl-9-(4-methoxy-2,3,6-trimethylphenyl)-2,4,6,8-nonatetraenoic Acid

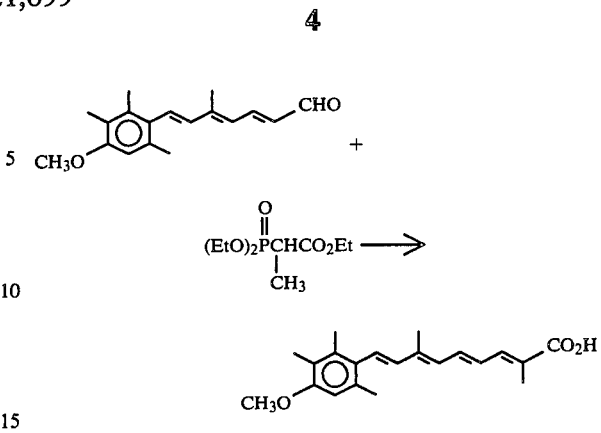

In a manner similar to Example 1, 7-(4-methoxy-2,3,6-trimethylphenyl)-5-methylhepta-2,4,6-trien-1-al (4 g, 0.014 mol) was treated wih triethyl 2-phosphonopropionate to give 2.6 g of the crude ethyl ester of the title compound as an oil. Hydrolysis with KOH (1 g, 0.018 mol) afforded 0.8 g of the title compound as yellow crystals (from ethyl acetate/ethyl ether): mp 167°–169° C. MS (EI): 326 (m+).

Compounds of the present invention were found to have potent activity in regulating the formation of lipoxygenase and as such possess therapeutic value in the treatment of inflammatory conditions and allergic responses such as anaphylaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 4,12-diHETE are chemotactic for human neutrophils and eosinophils, and may augment the inflammation process, 5-HPETE is known to be a precursor of slow-reacting substance of anaphylaxis (SRS-A). The SRS family of molecules, such leukotrienes B, C, and D, have been shown to be potent bronchoconstrictors (see, NATURE 288, 484–486 (1980).

The protocol that follows describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spoted on silica gel TLC sheets, which are developed with an ethyl acetate/isooctane/water acetic acid solvent system. The 5-HETE spots are visulaized with iodine, cut out and placed in scintillation vials for counting. After adjusting for the extraction efficiency, the amount (pmole)

of ]$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Table I shows the concentration required for inhibition of the 5-lipoxygenase pathway (5-Lox/I$_{50}$ μm) for compounds of the present invention.

TABLE I

| Inhibition of 5-Lipoxygenase | | |
| --- | --- | --- |
| Compound of Example | | Lox, Rat PMN(I$_{50}$ μm) |
| 2 | | 50 |
| 4 | | 17 |
| all trans retinoic acid | ⎫ | 90 |
| Ro 10 - 9359 | ⎬ Standard | 10 ± 17% |
| Ro 11 - 1430 | ⎭ | −11 ± 19% |

The therapeutic agents of this invention may be administered alone or in combination with pharmaceutically-acceptable carriers, the proporation of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is intramuscularly, intravenously or subcutaneously. For parenteral administration, they may be used in the form of a sterile solution containing other solutes, for example, enough saline or glucose to make the solution isotonic. When applied topically for treating skin disorders, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally.

What is claimed is:

1. A therapeutic composition for the treatment of inflammatory conditions and allergic responses in a human host, in combination with at least one pharmaceutically acceptable extender, a therapeutically effective amount of a compound of the formula

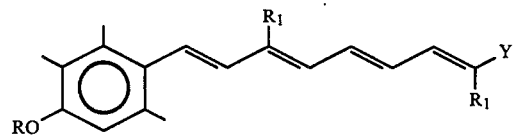

in which

R is H, lower alkyl of from 1 to 8 carbon atoms or aralkyl;

R$_1$ is H or lower alkyl from 1 to 5 carbon atoms; and

Y is carboxy, and pharmaceutically acceptable salts thereof.

2. A method for treating inflammatory conditions and allergic responses in a human host which comprises administering to said host a therapeutically effective amount of at least one compound of the formula

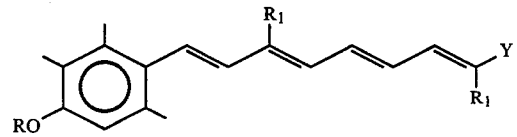

in which

R is H, lower alkyl of from 1 to 8 carbon atoms or aralkyl;

R$_1$ is H or lower alkyl of from 1 to 5 carbon atoms; and

Y is carboxy, and pharmaceutically acceptable salts thereof.

* * * * *